United States Patent [19]

Farhadieh et al.

[11] 4,013,820
[45] Mar. 22, 1977

[54] UNIVERSALLY USEABLE TABLETING INGREDIENTS

[75] Inventors: Bahram Farhadieh, Libertyville; James Maynard Berdahl, Gurnee, both of Ill.

[73] Assignee: Abbott Laboratories, North Chicago, Ill.

[22] Filed: Nov. 7, 1974

[21] Appl. No.: 521,989

[52] U.S. Cl. .................................. 536/64; 424/35; 424/181; 424/248.57; 526/317; 526/327; 526/329; 528/496; 536/3; 536/66

[51] Int. Cl.$^2$ .................. C08B 5/00; C08B 13/00

[58] Field of Search ............ 424/35; 260/224, 225; 536/64, 66; 528/496

[56] References Cited

UNITED STATES PATENTS

| 2,093,463 | 9/1937 | Malm et al. | 260/225 |
|---|---|---|---|
| 2,768,161 | 10/1956 | Malm et al. | 260/225 |
| 2,809,191 | 10/1957 | Sloan et al. | 260/225 |
| 2,852,508 | 9/1958 | Hiatt et al. | 260/225 |
| 2,865,898 | 12/1958 | Hiatt et al. | 260/225 |
| 3,080,294 | 3/1963 | Shepard | 260/225 |
| 3,424,842 | 1/1969 | Nurnborg | 424/94 |

OTHER PUBLICATIONS

Chem. Abst., 76 No. 103706h (1972) Golovkin et al., "Formulation of Enterosoluble Gelatin Capsules".
Chem. Abst., 77 No. 49594a (1972) Vavilin et al., "Use of Polymers for Improving Antibacterial Preparations".

*Primary Examiner*—Ronald W. Griffin
*Attorney, Agent, or Firm*—Paul D. Burgauer

[57] ABSTRACT

Known polymers of a defined class are converted into a universally useable tableting ingredient that provides controlled release of a drug from tablets made with this material. The new material is made in a rapidly stirred, nonaqueous solvent in a one-step process.

5 Claims, No Drawings

UNIVERSALLY USEABLE TABLETING INGREDIENTS

DETAILED DESCRIPTION OF THE INVENTION

Tableting media and coating compositions have been made from synthetic and partially natural polymers for many years. Numerous methods have previously been described for applying a polymer to tablets or to tableting ingredients to produce sustained release or enteric properties to tablets made therefrom.

Tablets made with enteric properties are designed to protect the active ingredient of the tablet from being exposed to the juices of the stomach. Sustained release tablets, on the other hand, are designed to provide a gradual release of a drug from the tablet over a prolonged period of time. None of these methods is applicable where it is desired that the release of the drug is solely controlled by the pH of the environment in order to avoid acid degradation of exposed drug particles and to provide protection from enzymatic degradation of drugs that might be vulnerable in this manner. Control of drug release is particularly desirable or mandatory, where the drug is more stable in a less acidic environment than that of the stomach and the drug molecule reaches a state of ionic equilibrium there which maximizes its absorption.

It is therefore an object of this invention to provide a method for protecting acid sensitive drug particles from degradation in an acidic environment without materially interferring with drug release in less acidic environments. It is another object of this invention to provide a controlled release of drug particles from an oral preparation whereby the release is controlled by the pH of the environment. It is a particular object of this invention to provide a method for protecting acid degradable drug particles which substantially completely protects said drug particles only during exposure thereof to an acidic environment. A still further object of this invention is the provision of a tableting medium in powdered form that can be used universally with any acid sensitive drug and by simply mixing said medium with such a drug for formulating the final drug form.

These and other objects are accomplished by the process of making a powdered, controlled-release tableting medium of essentially unlimited shelf-life consisting essentially in dissolving a nontoxic polymeric film-forming material having repeating free carboxylic acid groups attached to the polymeric chain in a low boiling organic liquid and combining this solution with solution of ammonia, sodium hydroxide or potassium hydroxide in an alcohol of 1 – 3 carbon atoms under conditions of turbulence over a period of at least 15 minutes and separating the formed polymer salt from the liquid phase by a method which does not require exposing said polymer salt to an extended period of heat.

The term "conditions of turbulence" is intended to refer to procedures which cause the reaction medium to be in a state of irregular flow at the site where the reaction between the components takes place. The salt formation reaction of the present process occurs instantly upon contact between the base and the polymer. The turbulence assures thorough dispersion of the base solution in the polymer solution and causes intimate contact between the acid sites on the polymer chain and the cation of the base. Consequently, turbulence has to be provided only temporarily at the reaction site. This can be accomplished by agitating the medium at a rate of at least 300 rpm and/or providing baffles in the reaction vessel that cause turbulence while the base is added to the polymer solution or by spraying the solution of one component in finely divided form into the agitated solution of the other component. In the latter instance, only moderate agitation speeds are required since the spray of the solution that is being added already is broken up into minute droplets containing very small portions of the reactant's particles.

The term "low boiling organic liquid" is intended to limit the materials to solvents having a boiling point of about 100° C. or less. This solvent preferably is miscible with the alcohol used as a solvent for the base. Agitation is preferably carried out for a period of at least 15 minutes and usually less than one hour since agitation beyond that period does not change the particle size or configuration.

The term "method which does not require exposing said polymer salt to an extended period of heat" is intended to include such well known methods as flash evaporation, lyophilization and in some circumstances, could also include high-vacuum distillation. The important aspect of this operation is the avoidance of any degradation of the polymer salt since the liquid phase contains, at this point, a small portion of water that formed during the reaction between the two components.

Operating in the above manner, the polymer salt is obtained directly in powdered form while other methods lead to a gummy product that must undergo several steps before a stable, useful powder is obtained. The new form of the polymer salt is substantially pure, i.e., no degradation has taken place since exposure to any deteriorating liquid has been minimized. Also, the formed particles are small and are substantially free of any entrapped liquid. This provides for a stable, powdered product that can be stored essentially for unlimited periods of time under proper and normal storage conditions. These particles can then just be combined with active drugs and the usual tableting ingredients to produce tableting formulations which produce a tablet that has the controlled-release aspect often required when a drug is administered that is irritating to parts of the G.I. tract and/or has to be metered over an extended period into the G.I. tract or an acid or stomach enzyme sensitive drug. The above powder has the further advantage that it can be used also in the preparation of drug particles or granules intended for use in suspensions or other common types of drug forms such as syrups, wafers, pills and the like.

Depending on the choice of polymer, the powdered product of the present invention can be designed to provide controlled release at a given range of pH. When cellulose acetate phthalate (hereinafter referred to as CAP) is used in connection with sodium hydroxide, the pH solubility is at 5.5 or above; using hydroxypropylmethylcellulose phthalate, the solubilizing pH is about 5; and using a copolymer of methacrylic acid and methacrylic acid loweralkyl ester, the pH solubility can be prechosen to be above 6.0 or 7.0 depending on the type and proportion of the methacrylic acid ester in this copolymer.

In order to illustrate the process of the present invention, reference is made to the following examples which are not intended to limit the invention in any respect.

EXAMPLES 1 – 8

In a Cowles dispensator, a solution of 75 g. of CAP in the indicated solvent was agitated at 3000 rpm (2080 ft./min.) using a spatula as a baffle to further improve agitation. A solution of 13.5 g. of sodium or 19.5 g. of potassium hydroxide in 300 ml. of the indicated solvent was added thereto over a period of 30 – 75 minutes as shown under the heading of "time" below. Stirring was continued 15 minutes beyond this, followed by filtration. The results are given below, showing the yield after vacuum drying.

TABLE I

| Ex. No. | CAP Solvent | Base | Time | Yield* |
|---|---|---|---|---|
| 1 | Acetone | KOH | 50 Min. | 68.7 g. |
| 2 | Acetone | KOH | 75 Min. | 78.5 g. |
| 3 | Acetone | NaOH | 50 Min. | 66.4 g. |
| 4 | Acetone | NaOH | 70 Min. | 69.1 g. |
| 5 | $CH_3COC_2H_5$ | KOH | 45 Min. | 70.9 g. |
| 6 | $CH_3COC_2H_5$ | NaOH | 45 Min. | 66.4 g. |
| 7 | $CH_3OH:CH_2Cl_2$ 1:1 | KOH | 30 Min. | 61.8 g. |
| 8 | $CH_3OH:CH_2Cl_2$ 1:1 | NaOH | 45 Min. | 64.5 g. |

*In these examples, no attempt was made to optimize the yield as material adhering to the side of the reaction vessel was not recovered.

The CAP salts obtained in powdered form by these variations were all found to be stable and free of entrapped solvents; essentially no degradation was observed upon storing these powders under normal storage conditions.

When the procedure of Example 1 was repeated but using ammonia in ethanol for salt formation, the polymer salt was obtained in physical form and density substantially identical to the material of Example 1.

EXAMPLE 9

In a repetition of the process of Example 7, the effect of the agitation speed was varied between 500 and 3000 rpm (tip speed of 345 – 2772 ft./min.) with addition times of 35 – 45 minutes. The yields of precipitated potassium CAP were checked as in the above examples; they varied from 67.9 to 73.8 g. In all instances, the product was a finely divided powder after vacuum drying and retained its chemical and physical properties upon storage.

EXAMPLE 10

In a repetition of Example 9 but using an ordinary laboratory glass beaker with a 4-inch glass stirrer at 515 rpm, but no baffle and no other cause of turbulence, the ensuing product contained many semisoft, semisolid agglomerates before vacuum drying. Upon drying, the material was less dense than that of the various runs in Example 9. This clearly indicated the presence of considerable amounts of solvents before and after drying and proved the necessity of an irregular flow during the salt formation process.

EXAMPLES 11 – 16

An aqueous sodium CAP solution made according to the method of Example 8 was freeze-dried and the dried material was milled to a powder passing through a 30-mesh screen. This powder was intimately blended with chlorazepate dipotassium (Chl.-$K_2$) containing the below indicated amount of potassium chloride or carbonate. The powder blends were compressed at 800 psi on a Carver Press into 300 mg. tablets using 13/32-inch flat surface punches and dies. The composition, variations (Table II) and resulting properties in simulated gastric fluid (Table III) of these tablets are listed below. All assays were done by standard laboratory test procedures under conditions indicated.

TABLE II

| Ex. No. | Chl.-$K_2$ | NaCAP | $K_2CO_3$ | KCl |
|---|---|---|---|---|
| 11 | 50 mg. | 250 mg. | 0 | 0 |
| 12 | 25 mg. | 210 mg. | 15 mg. | 50 mg. |
| 13 | 25 mg. | 160 mg. | 15 mg. | 100 mg. |
| 14 | 25 mg. | 110 mg. | 15 mg. | 150 mg. |
| 15 | 25 mg. | 60 mg. | 15 mg. | 200 mg. |
| 16 | 25 mg. | 30 mg. | 15 mg. | 230 mg. |

TABLE III

| Ex. No. | 11 | 12 | 13 | 14 | 15 | 16 |
|---|---|---|---|---|---|---|
| 15 Min. | 7 | 8 | 8 | 11 | 15 | 33 |
| 30 Min. | 11 | 11 | 11 | 17 | 22 | 49 |
| 60 Min. | 17 | 15 | 19 | 24 | 30 | 60 |
| 90 Min. | | 19 | 26 | 28 | 35 | 68 |
| 120 Min. | 23 | 22 | 29 | 31 | 42 | 75 |
| 180 Min. | 29 | 28 | 34 | 38 | 49 | 85 |
| 240 Min. | 33 | 31 | 37 | 42 | 54 | 91 |

The numbers shown in Table III represent the amount of the active drug (Chl.-$K_2$) present that went into solution at 25° C. They clearly indicate the controlled release of drug over a considerable time span with fairly even portions of the drug being released during each time period, irrespective of the presence of other water soluble salts which only increase the release/time rate without substantial changes in the release pattern.

EXAMPLE 17

The tablet of Example 11 was tested as in the previous examples except that simulated intestinal fluid was used as the release medium (pH 7.5). The release of drug amounted to 20% by weight of drug present in 15 Minutes, 40% in 30 Minutes, 80% in 1 hour and 100% in 2 hours.

EXAMPLE 18

The tablet of Example 11 was first allowed to leach in simulated gastric fluid for 1 hour and was then placed in simulated intestinal fluid. The amount of drug released after 1-½ hours (1 hour in gastric, one-half hour in intestinal fluid) amounted to 28%. After 2 hours and 3 hours, the drug was released in amounts of 54% and 100%, respectively.

EXAMPLES 19 – 21

Different amounts of erythromycin A base were dispersed in 100-ml. portions of a 9.5% wt./vol. aqueous solution of NaCAP. The mixtures were freeze-dried over night to white fluffy cakes which were pulverized and passed through a 30-mesh screen. The time required to dissolve 1 g. of each sample in three different media of 100 ml. each was determined. The results are shown in Table IV.

TABLE IV

| Ex. No. | Ery. Base | Medium A | Medium B | Medium C |
|---|---|---|---|---|
| 19 | 291 mg. | insol. | <10 Min. | <10 Min. |
| 20 | 450 mg. | insol. | <10 Min. | <10 Min. |

TABLE IV-continued

| Ex. No. | Ery. Base | Medium A | Medium B | Medium C |
| --- | --- | --- | --- | --- |
| 21 | 551 mg. | insol. | <10 Min. | <10 Min. |

Medium A was simulated gastric fluid without pepsin, pH 1.2; Medium B was a 0.10 normal phosphate buffer, pH 5.5 and Medium C was simulated intestinal fluid without pancreatin, pH 7.5. Table IV shows that the active drug remains undissolved in stomach fluid while being released promptly at a pH substantially higher than that of the stomach, i.e., the pH of intestinal fluid.

EXAMPLE 22

In accordance with Example 11, tablets were compressed at 700 psi. of the compositions of Examples 19 – 21. Each tablet weighed 300 mg. and had a thickness of about 3 mm. The drug release of the tablets was studied at various pH levels, using a Pernarowski apparatus with 100 rpm stirring at 25° C. Assays were made by the arsino-molybdate method. The amount of drug released is expressed in Table V as percentage of the amount of drug present, using media A, B and C of Table IV.

TABLE V

| Composition Of Examples | 19 | 20 | 21 |
| --- | --- | --- | --- |
| Medium A 2 Hrs. | 17% | 22% | 39% |
| Medium A 4 Hrs. | 20% | 29% | 47% |
| Medium A 6 Hrs. | 23% | 36% | 53% |
| Medium B 1/2 Hr. | 18% | 13% | 8% |
| Medium B 2 Hrs. | 54% | 37% | 26% |
| Medium B 4 Hrs. | 96% | 65% | 49% |
| Medium B 6 Hrs. | 100% | 88% | 70% |
| Medium C 1/2 Hr. | 15% | 10% | 13% |
| Medium C 2 Hrs. | 70% | 46% | 54% |
| Medium C 4 Hrs. | 93% | 90% | 89% |
| Medium C 6 Hrs. | 100% | 100% | 100% |

While the above examples clearly demonstrate the controlled release and substantial protection of the drug from release in the stomach, using the particles of NaCAP and K-CAP made by the method of this invention, similar protection and release patterns can be demonstrated by using other polymer salt particles. The pH at which the drug is desired to be released can be preselected by choosing the polymer salt with which the drug is coated: the polymer salts made from Eudragit L (methacrylic acid - methacrylic acid ester copolymer) dissolves at a pH >6.0; Eudragit S (same components, but higher ester content) dissolves at pH >7.0; and the sodium salt of hydroxypropylmethylcellulosephthalate dissolves at >5.0. Polyacrylic acid, copolymers thereof, and copolymers of maleic anhydride such as with styrene, methyl vinyl ether, ethylene or the like or polymeric alginic acid are equally useful for the formation of the salt particles used herein. In each instance, the salts can be made by the above process and obtained directly in the form of a stable powder that does not deteriorate under proper storage conditions. In contrast thereto, polymer salts made by using water as the reaction medium are not obtained in powdered form as the salts are soluble and must then be carefully separated therefrom in order to minimize degradation.

Under the conditions of turbulence in accordance with this invention, the polymer salt particles are obtained directly in powdered form, entrapping substantially none of the reaction medium which contains a very small percentage of water due to the salt forming reaction. Drying of the polymer salt at low temperature in vacuo, lyophilization or other flash evaporation methods will assure that no deterioration can take place before even the last traces of water have been removed.

What is claimed is:
1. The process of making a powdered, controlled-release tableting medium of essentially unlimited shelf-life consisting essentially in dissolving a nontoxic polymeric film-forming material having repeating free carboxylic acid groups attached to the polymeric chain in a low boiling, substantially water-free organic liquid and combining this solution with a solution of ammonia, sodium hydroxide or potassium hydroxide in an alcohol of 1 – 3 carbon atoms under conditions of turbulence over a period of at least 15 minutes and separating the formed polymer salt from the liquid phase by a method which does not require exposing said polymer salt to an extended period of heat.
2. The process of claim 1 wherein said film-forming material is cellulose acetate phthalate.
3. The process of claim 1 wherein a solution of sodium hydroxide is used.
4. The process of claim 1 wherein said alcohol is ethanol.
5. A powdered, controlled-release tableting medium for pharmaceutical tablets consisting essentially of a film-forming, non-toxic polymeric material carrying in each repeating monomeric unit a carboxylic acid salt group selected from the group consisting of ammonium, potassium and sodium carboxylates, said powdered tableting medium being characterized in that it contains essentially no heat degradation product, no entrapped solvent and possessing essentially unlimited shelf-life.

* * * * *